(12) United States Patent
Huiku (10) Patent No.: US 8,401,605 B2
(45) Date of Patent: Mar. 19, 2013

(54) MULTIPLE WAVELENGTH PHYSIOLOGICAL MEASURING APPARATUS, SENSOR AND INTERFACE UNIT FOR DETERMINATION OF BLOOD PARAMETERS

(75) Inventor: Matti Huiku, Espoo (FI)

(73) Assignee: General Electric Company, Schenectady, NY (US)

( * ) Notice: Subject to any disclaimer, the term of this patent is extended or adjusted under 35 U.S.C. 154(b) by 993 days.

(21) Appl. No.: 12/432,982

(22) Filed: Apr. 30, 2009

(65) Prior Publication Data

US 2010/0280342 A1 Nov. 4, 2010

(51) Int. Cl.
*A61B 5/1455* (2006.01)
(52) U.S. Cl. .................. 600/322; 600/310; 600/323
(58) Field of Classification Search ............ 600/310, 600/322, 323, 324, 326, 331, 344, 473, 476
See application file for complete search history.

(56) References Cited

U.S. PATENT DOCUMENTS

| | | | |
|---|---|---|---|
| 4,819,752 A * | 4/1989 | Zelin | 600/322 |
| 6,104,938 A | 8/2000 | Huiku et al. | |
| 2006/0211924 A1 | 9/2006 | Dalke et al. | |
| 2006/0211932 A1* | 9/2006 | Al-Ali et al. | 600/344 |
| 2006/0220881 A1* | 10/2006 | Al-Ali et al. | 600/310 |
| 2006/0241363 A1 | 10/2006 | Al-Ali et al. | |
| 2007/0149865 A1* | 6/2007 | Laakkonen | 600/310 |
| 2008/0183232 A1 | 7/2008 | Voss et al. | |

FOREIGN PATENT DOCUMENTS

| | | |
|---|---|---|
| WO | 01/52727 A1 | 7/2001 |
| WO | 2007143626 A2 | 12/2007 |

OTHER PUBLICATIONS

EP Search Report and Written Opinion from corresponding EP Application No. 10188935.0, Mar. 1, 2011.

* cited by examiner

*Primary Examiner* — Eric Winakur
*Assistant Examiner* — Chu Chuan (JJ) Liu
(74) *Attorney, Agent, or Firm* — Andrus, Sceales, Starke & Sawall, LLP (57) ABSTRACT

A measuring apparatus, a physiological sensor, and an interface unit for determining blood parameters of a subject are disclosed. The sensor comprises an emitter unit comprising a first plurality of emitter elements configured to emit radiation at a second plurality of wavelengths and a detector unit configured to receive radiation generated by the emitter elements and transmitted through the tissue of the subject, wherein the detector unit is further configured to produce electric measurement signals indicative of absorption caused by the blood of the subject. The sensor or the interface unit is provided with a memory that stores emitter activation information for at least a third plurality of wavelengths, thereby to enable a monitoring unit operably connectable to the physiological sensor to employ a combination of wavelengths selected from the third plurality of wavelengths, wherein the third plurality is equal to or smaller than the second plurality.

20 Claims, 4 Drawing Sheets

MULTIPLE WAVELENGTH PHYSIOLOGICAL MEASURING APPARATUS, SENSOR AND INTERFACE UNIT FOR DETERMINATION OF BLOOD PARAMETERS

BACKGROUND OF THE INVENTION

This disclosure relates to multiple optical wavelength physiological sensors and monitors, especially to pulse oximeters.

Pulse oximetry is a well-established technique for measuring oxygen saturation ($SpO_2$) in arterial blood. $SpO_2$ is an important parameter that relates to the adequacy of oxygen supply to peripheral tissues and organs. Pulse oximeters provide instantaneous in-vivo measurements of arterial oxygenation, and thereby an early warning of arterial hypoxemia, for example. Pulse oximeters also display a photoplethysmographic (PPG) pulse waveform, which can be related to tissue blood volume and blood flow, i.e. the blood circulation, at the site of the measurement, typically in finger or ear. Standard pulse oximeters use two wavelengths to measure the ratio of oxyhemoglobin to total functional hemoglobin, indicated as an $SpO_2$ value. However, pulse oximeters using more than two wavelengths have also been developed to be able to non-invasively measure the levels of the other blood substances that provide important clinical information. For example, levels of other significant hemoglobin species, such as carboxyhemoglobin and methemoglobin, and total hemoglobin may be estimated if the number of wavelengths used in the pulse oximeter is increased.

Since the measurement is normally made from an anatomical extremity, such as a finger tip, pulse oximeters typically comprise a separate sensor attachable to a subject and the actual pulse oximeter device to which the sensor is connected through a cable. The sensor normally comprises two or more emitter elements, each emitting radiation at a specific wavelength, and a broad spectral band photodetector common to all emitter elements. Due to the various combinations of wavelengths that may be used to measure certain substances in blood and the variety of sensor types needed for different subjects and different measurement sites, the choice of sensors and interface cables that may be used in connection with one pulse oximeter device may be rather extensive. The different sensors along with the different cables and/or connectors to be used in connection with the said sensors make the operation of a pulse oximeter device rather demanding thus detracting from the user-friendliness of the device.

This drawback is further aggravated by the fact that the current oximeters do not inform the user about possible incompatibility and accuracy issues the user may encounter while using an incompatible sensor or a sensor that has degraded in performance.

While a certain measurement mode, i.e. the combination of wavelengths used, normally requires a particular sensor compatible with the mode, the internal operation of a measurement mode is normally fixed in terms of the utilization of the wavelengths, which may reduce the signal-to-noise ratio and the accuracy of the some measurements.

BRIEF DESCRIPTION OF THE INVENTION

The above-mentioned problems are addressed herein which will be comprehended from the following specification.

In an embodiment, a measuring apparatus for determining the amount of at least one substance in blood of a subject comprises a sensor unit comprising (1) an emitter unit comprising a first plurality of emitter elements configured to emit radiation at a second plurality of wavelengths and (2) a detector unit configured to receive radiation generated by the emitter elements and transmitted through tissue of a subject, wherein the detector unit is further configured to produce electric measurement signals indicative of absorption caused by blood of the subject. The apparatus further comprises a first memory storing emitter activation information for at least a third plurality of wavelengths, wherein the third plurality of wavelengths belongs to the second plurality of wavelengths, and a monitoring unit configured to process the electric measurement signals, wherein the monitoring unit is further configured to produce, based on the emitter activation information, control information for employing a desired combination of wavelengths selected from the third plurality of wavelengths.

In another embodiment, a physiological sensor for use in determining the amount of at least one substance in blood of a subject comprises (1) an emitter unit comprising a first plurality of emitter elements configured to emit radiation at a second plurality of wavelengths and (2) a sensor memory storing emitter activation information for at least a third plurality of wavelengths, thereby to enable a monitoring unit operably connectable to the physiological sensor to employ a desired combination of wavelengths selected from the third plurality of wavelengths, wherein the third plurality of wavelengths belongs to the second plurality of wavelengths. The physiological sensor further comprises a detector unit configured to receive radiation generated by the emitter elements and transmitted through tissue of the subject, wherein the detector unit is further configured to produce electric measurement signals indicative of absorption caused by blood of the subject.

In a still further embodiment, an interface unit for use in determining the amount of at least one substance in blood of a subject comprises a first interface for connecting the interface unit to a monitoring unit, a second interface for connecting the interface unit to a sensor unit comprising a first plurality of emitter elements configured to emit radiation at a second plurality of wavelengths, and an emitter switching unit configured to connect drive current generated by the monitoring unit to the sensor unit through the second interface. The interface unit further comprises a memory storing emitter activation information for at least a third plurality of emitter elements, thereby to enable the monitoring unit to employ a desired combination of wavelengths selected from the third plurality of wavelengths, wherein the third plurality of wavelengths belongs to the second plurality of wavelengths.

Various other features, objects, and advantages of the invention will be made apparent to those skilled in the art from the following detailed description and accompanying drawings.

DETAILED DESCRIPTION OF THE INVENTION

Figure 1:
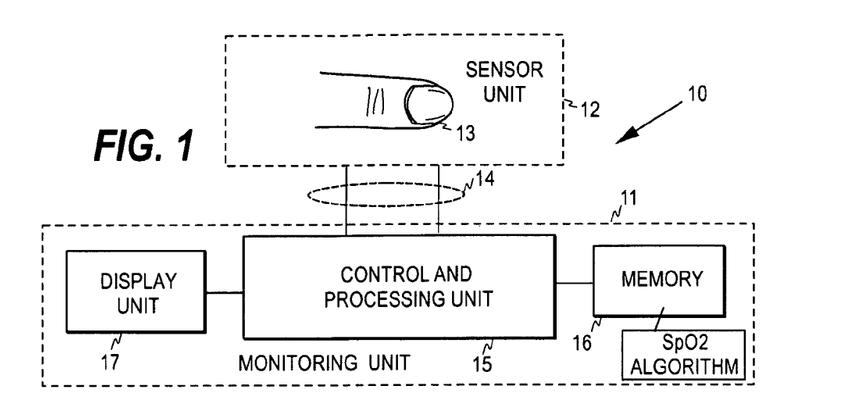
FIG. 1 is a block diagram illustrating the basic configuration of a conventional pulse oximeter.

FIG. 1 illustrates the basic elements of a conventional pulse oximeter 10. A pulse oximeter normally comprises a bedside monitoring unit 11 and a probe or sensor unit 12 attachable to a subject, typically to a finger 13 or ear lobe of the subject. The sensor unit is normally connected to the monitoring unit through a cable 14. The monitoring unit may be conceived to comprise three basic elements: a computerized control and processing unit 15, a memory 16 for the control and processing unit, and a display 17 for displaying information to a user of the pulse oximeter.

The sensor unit normally includes light sources for sending optical signals through the tissue and a photodetector for receiving the signals transmitted through or reflected from the tissue. On the basis of the transmitted and received signals, light absorption by the tissue may be determined. During each cardiac cycle, light absorption by the tissue varies cyclically. During the diastolic phase, absorption is caused by venous blood, non-pulsating arterial blood, cells and fluids in tissue, bone, and pigments, whereas during the systolic phase there is an increase in absorption, which is caused by the inflow of arterial blood into the tissue part on which the sensor is attached. Pulse oximeters focus the measurement on this pulsating arterial blood portion by determining the difference between the peak absorption during the systolic phase and the background absorption during the diastolic phase. Pulse oximetry is thus based on the assumption that the pulsatile component of the absorption is due to arterial blood only.

In order to distinguish between two species of hemoglobin, oxyhemoglobin ($HbO_2$) and deoxyhemoglobin (RHb), absorption must be measured at two different wavelengths, i.e. the sensor of a traditional pulse oximeter includes two different light emitting diodes (LEDs) or lasers. The wavelength values widely used are 660 nm (red) and 940 nm (infrared), since the said two species of hemoglobin have substantially different absorption at these wavelengths. Each LED is illuminated in turn at a frequency which is typically several hundred Hz. If the concentrations of more than said two hemoglobin species are to be evaluated, more than two wavelengths are needed. Such a pulse oximeter is here termed a multiwavelength pulse oximeter.

The light propagated through or reflected from the tissue is received by a photodetector, which converts the optical signal received at each wavelength into an electrical signal pulse train and feeds it to an input amplifier. The amplified signal is then supplied to the control and processing unit 14, which converts the signals into digitized format for each wavelength channel. The digitized signal data is then utilized by an $SpO_2$ algorithm. The control and processing unit executes the algorithm and drives the display 16 to present the results on the screen thereof. The $SpO_2$ algorithm may be stored in the memory 15 of the control and processing unit. The digitized photoplethysmographic (PPG) signal data at each wavelength may also be stored in the said memory before being supplied to the $SpO_2$ algorithm. With each LED being illuminated at the above-mentioned high rate as compared to the pulse rate of the subject, the control and processing unit obtains a high number of samples at each wavelength for each cardiac cycle of the subject. The time windows corresponding to a particular wavelength are often referred to as a wavelength channel.

For addressing the above-mentioned problems, a multi-wavelength pulse oximeter comprises a sensor unit and a monitoring unit that may be connected to the sensor unit directly (through a cable) or through an optional interface unit. The sensor unit includes a memory including emitter activation information that enables the oximeter device (monitoring unit) to employ any desired combination of wavelengths available in the sensor, using optimal time division multiplexing of the wavelength channels. As discussed below, the emitter activation information may also be stored in a separate interface module provided with an emitter switching unit and connected between the sensor unit and the monitoring unit. The content of the emitter activation information may vary depending on the way the monitoring unit uses the said information to obtain the actual control information that it needs to be able to generate the wavelength channels for the desired combination of wavelengths.

Figure 2:
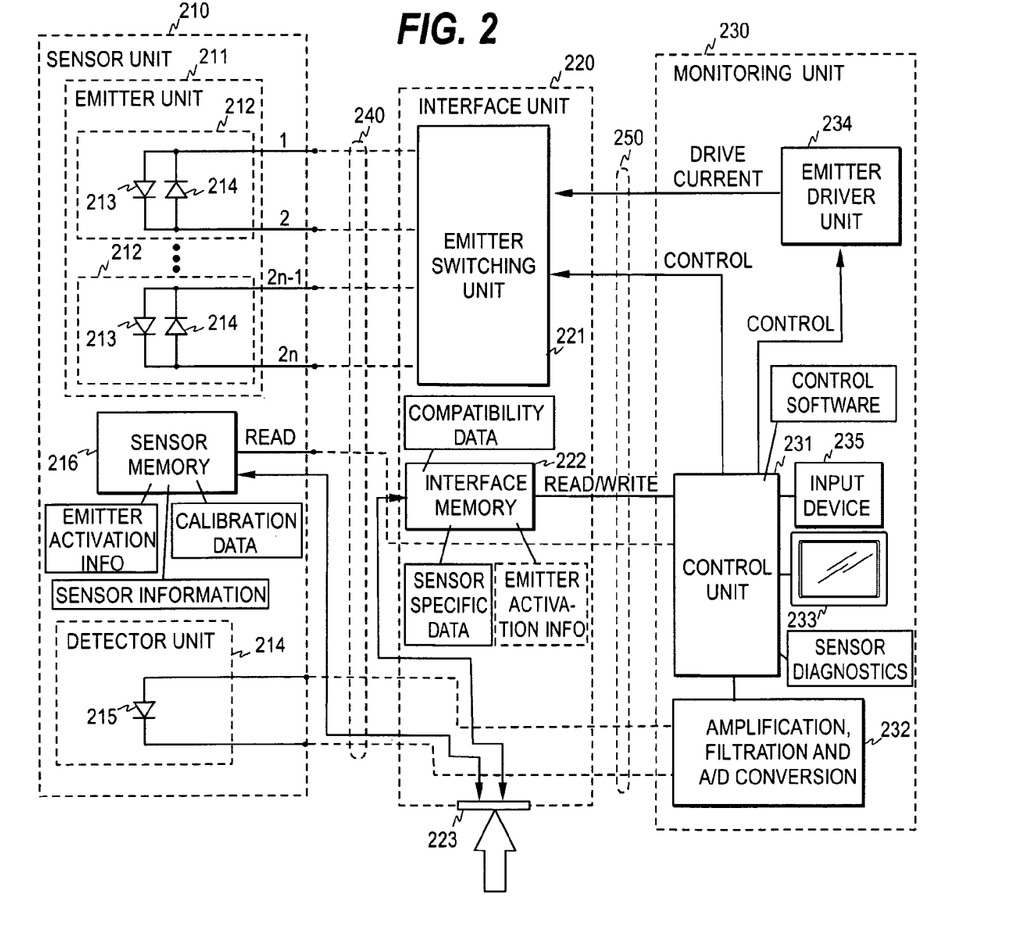
FIG. 2 illustrates an embodiment of a multiwavelength pulse oximeter.

FIG. 2 illustrates one embodiment of a multiwavelength pulse oximeter for addressing the above-mentioned problems. The sensor unit 210 is in this case connected to the monitoring unit 230 through an interface unit 220 which in this example includes an emitter switching unit 221 and a memory 222. The interface unit 220 is in this example a separate module connected to the monitoring unit 230 through a connector 250. However, the interface unit may also be integrated with the monitoring unit 230 or with the cable 14. The element 240 connecting the interface unit to the sensor unit may thus comprise a connector and/or a cable. As discussed below, the interface unit serves to facilitate a use of different types of sensors without making the actual monitoring unit too complex. The interface unit also facilitates a modular multiwavelength design, in which the monitoring unit 230 may include only essential signal processing for the different possible signal trains and one electric current source unit that can serve multiple light sources. The interface unit may or may not be provided with a dedicated memory, regardless of whether the unit is a separate module or integrated with the monitoring unit or the cable.

The sensor unit 210 of FIG. 2 comprises an emitter unit 211 comprising n ($n \geq 2$) emitter element units 212 each comprising two emitter elements (LEDs or lasers) 213, 214 connected in parallel and back-to-back, i.e. in each emitter element unit the anode of the first emitter element and the cathode of the second emitter element are connected together and form a first common pole, while the cathode of the first emitter element and the anode of the second emitter element are connected together to form a second common pole. The said poles form the terminals of one emitter element unit 212, while the terminals of all emitter element units form the terminals of the emitter unit. As illustrated in the figure, the total number of the said terminals is 2n in this embodiment. Each emitter element is adapted to emit radiation at a dedicated wavelength, i.e. the number of wavelengths may also be 2n. However, the number of wavelengths may also be lower, if all units 212 do not include two emitter elements or if two or more units 212 comprise substantially the same wavelengths. Furthermore, as discussed below in connection with FIG. 5, the n emitter element units may also be cascaded. In this embodiment, the total number of terminals is n+1, but the number of wavelengths may still be 2n, if all emitter element units include two emitter elements and all emitter elements have different wavelengths.

The sensor unit further comprises a sensor memory 216 and a detector unit 214 comprising a broad spectral band photodetector 215 adapted to receive the radiation emitted by the emitter elements and to convert the optical signals into electric signals.

In the monitoring unit 230, the control and processing unit and the associated memory is illustrated as a control unit 231. In addition to the above basic elements, the monitoring unit of FIG. 2 comprises a reception branch 232 adapted to receive the electric signals from the photodetector and an emitter driver unit 234 adapted to generate, under the control of the control unit, drive current for the emitter elements. The reception branch 232 typically comprises an input amplifier, a band-pass filter, and an A/D converter (not shown). The digitized signal output from the A/D converter is supplied to the control unit 231, which processes the signal data and displays the analysis results on the screen of a display unit 233. The control unit is provided with control software for controlling the activation of the emitter elements in the emitter element units by controlling the emitter driver unit 234 and the emitter switching unit 221 in a synchronized manner. Therefore, the control unit also knows from which one of the emitter elements the signal data originates in each time window. The drive current generated in the emitter driver unit is supplied to the emitter switching unit 221. The control unit controls the switches of the emitter switching unit so that a repeating drive pulse sequence is generated, each pulse thereof being supplied to the correct emitter element (i.e. LED or laser). The required control information may be produced based on the emitter activation information stored in sensor memory 216.

Sensor memory 216 may store various information about the sensor. In this embodiment, the information may be divided into three categories: sensor information, calibration data, and emitter activation information. The sensor information includes sensor-specific data, such as the type (finger/ear/adult/infant/neonatal, etc.) or the specified use (total hemoglobin, carboxyhemoglobin, methemoglobin or standard SpO2 measurement) and the identifier of the sensor in question. The identifier may be, for example, the serial number of the sensor. The sensor information may further include history data indicative of the total time the sensor has been in operation. This information may be updated by the control unit 231 each time the sensor has been used. The calibration data may include various data that the measurement algorithms stored in the control unit may utilize. For example, the calibration data may include the following data: extinction coefficient data, center wavelengths used in the sensor, temperature coefficients for wavelength temperature shift, nominal tissue parameters at calibration conditions, and sensor optics and design characteristics, such as sensor nominal current transfer ratios. The extinction coefficient data includes the extinction coefficients related to each wavelength/blood substance pair, i.e. each extinction coefficient indicates the absorption of the said blood substance at the wavelength in question. The temperature coefficients indicate how the center wavelengths change as a function of temperature and the tissue parameters indicate, for instance, how the transmission in the tissue affects the spectral characteristics seen by the detector, i.e. how the tissue shifts the center wavelength. The current transfer ratios (CTRs) indicate the ratio of the detector output current to the LED input current for each LED/detector pair while there is no tissue between the detector and the LEDs.

The emitter activation information stored in the sensor memory includes information indicating how the emitter unit is to be driven to generate an optical signal at a desired wavelength. The said information may be combined with the extinction coefficient data. The combined information may be in the form of a table as is shown in Table 1 below.

TABLE 1

| Terminals | Current polarity | RHb | HbO2 | HbCO | HbMet | HbX | Center Wavel. (nm) |
|---|---|---|---|---|---|---|---|
| 1, 2 | Plus | $\epsilon_{RHb,632}$ | $\epsilon_{HbO2,632}$ | $\epsilon_{HbCO,632}$ | $\epsilon_{HbO2,632}$ | $\epsilon_{HbX,632}$ | 632 |
| 1, 2 | Minus | $\epsilon_{RHb,660}$ | $\epsilon_{HbO2,660}$ | $\epsilon_{HbCO,660}$ | $\epsilon_{HbO2,660}$ | $\epsilon_{HbX,660}$ | 660 |
| 3, 4 | ... | ... | ... | ... | ... | ... | ... |
| ... | ... | ... | ... | ... | ... | ... | ... |
| 2n − 1, 2n | Minus | $\epsilon_{RHb,940}$ | $\epsilon_{HbO2,940}$ | $\epsilon_{HbCO,940}$ | $\epsilon_{HbO2,940}$ | $\epsilon_{HbX,940}$ | 940 |

In table 1, the first, second and last columns indicate how the emitter unit is to be driven to generate a signal at a specific wavelength. The first row of the said columns indicates that if a drive current is supplied from terminal 1 to terminal 2 (i.e. positive current with respect to terminals 1 and 2), a signal having a center wavelength of 632 nm is generated. Similarly, the second row of the said columns indicates that if a drive current is supplied in the opposite direction between terminals 1 and 2 of the emitter unit (i.e. negative current with respect to terminals 1 and 2), an optical signal having a center wavelength of 660 nm is generated. Columns 3-7 of table 1 include, respectively, the extinction coefficients of deoxyhemoglobin (RHb), oxyhemoglobin (HbO$_2$), carboxyhemoglobin (HbCO), methemoglobin (metHb), and one further hemoglobin species (HbX) at the wavelengths used in the emitter unit. It is assumed in table 1 that the shortest wavelength is 632 nm and the longest 940 nm, and that the emitter unit is provided with 2n drive input terminals.

The content of the sensor memory may depend on whether or not the interface unit is provided with a dedicated memory. If there is no memory in the interface unit, the information that enables the control unit to activate a desired combination of emitter elements is in the sensor memory. As above, this information may directly indicate, for each wavelength, the input terminals of the sensor unit and polarity of current to be supplied to said terminals. However, the emitter activation information in the sensor memory may also be in the form of control codes, for example, in which case the control unit may map each code to the control information needed to employ a particular set of wavelengths. However, if the interface unit is provided with a dedicated memory, the said memory may store the emitter activation information or part of it.

Figure 3:
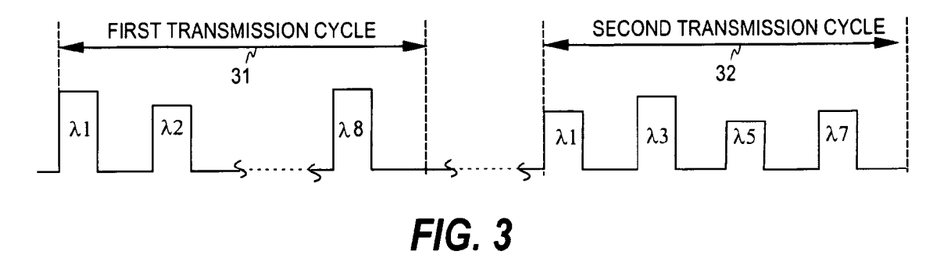
FIG. 3 illustrates the drive pulse sequences of two measurement modes of the multiwavelength pulse oximeter of FIG. 2.

Control unit 231 may read the content of sensor memory 216 through the interface unit, thereby to obtain information on how each wavelength is to be generated. Thus, as a certain measurement to be carried out by the control unit requires a specific set of wavelengths, the control unit may determine, based on the emitter activation information, the control information that may be used to activate the required LEDs only. FIG. 3 illustrates the repeating drive pulse sequences 31, 32 for two measurements. In the first measurement, 8 wavelengths are needed for the measurement, which are in this example wavelengths λ1-λ8. The control unit therefore produces control information that controls the emitter driver unit 234 and the emitter switching unit 221 so that the LEDs corresponding to wavelengths λ1-λ8 are activated in desired order using an appropriate drive current for each LED. In the second measurement, four wavelengths are needed, which are in this example wavelengths λ1, λ3, λ5, and λ7. Again, the control unit may determine, based on the emitter activation information, the control information needed to activate the required LEDs only, as is shown in FIG. 3. Thus, in FIG. 3 the wavelength marks within each drive pulse indicate that at that time slot the control information supplied by the control unit to the emitter switching unit 221 is such that only the LED corresponding to that wavelength is activated. Consequently, the number of pulse in each repeating pulse sequence corresponds to the number of wavelengths needed. However, as mentioned above, the wavelengths may be activated in a desired order within the pulse sequence.

The above LED control modes, which activate the required LEDs only, enable optimal time division multiplexing of the wavelength channels that are needed for the measurement. Furthermore, as the combination of wavelengths may be selected flexibly using the emitter activation information, the combination of the wavelengths employed may be changed dynamically over time. For example, the dynamical alternation of the combination may depend on the blood parameters to be tracked and on the rate at which the said parameters may change; parameters that may change faster may be measured more frequently than parameters having a slower rate of change. The above features improve the signal-to-noise ratio and, thereby, accuracy of the particular measurement. The above control modes may also be sensor-specific: the control unit may use one or more LED control modes for one sensor type and one or more other control modes for another sensor type. In this case the emitter activation information in the sensor memory 216 may comprise the control codes for the control modes compatible with the sensor. The control unit may retrieve the control code corresponding to the wavelength combination to be employed and use the retrieved control code to produce the control information for the corresponding LEDs. The emitter activation information may thus include the required information for each emitter element separately, as in table 1, or for each wavelength combination possible with the sensor. The information may also be in the form of access codes that the control memory may use to retrieve the required information from another location, such as from the memory of the control unit.

Figure 4:
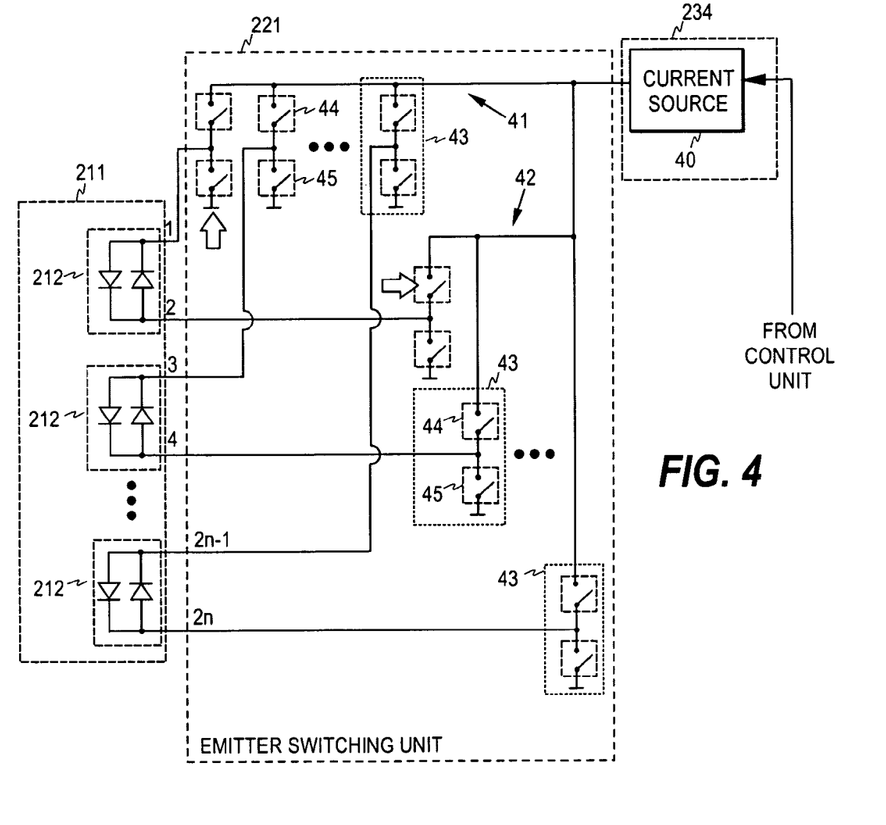
FIG. 4 illustrates an example of the emitter switching unit and emitter driver unit of the embodiment of FIG. 2.

FIG. 4 illustrates one embodiment of the emitter driver unit 234 and the emitter switching unit 221 of FIG. 2. For reasons of clarity, other elements except emitter unit 211 have been omitted in the figure. The emitter current source comprises in this example a single current source 40, which outputs the drive current for the pulse sequences of FIG. 3. In this embodiment, drive current for the first emitter elements (LEDs) in all emitter element units 212 is supplied through output branch 41, while the drive current for the second emitter elements (LEDs) in all emitter element units is supplied through output branch 42. In other words, current source 40 is connected to the anodes of the first emitter elements (LEDs) in the emitter element units through output branch 41, and to the anodes of the second emitter elements (LEDs) of the emitter element units through output branch 42. The connection is formed through the emitter switching unit, which comprises n switching units 43 in each output branch. Each of the 2n switching units 43 comprises a first switching element 44 and a second switching element 45 connected in series. If, for example, the emitter activation information indicates that wavelength λ2 is to be produced by supplying current from terminal 2 to terminal 1 of the emitter unit, the control unit generates, in the time slot corresponding to wavelength λ2, a drive pulse amplitude suitable for the corresponding LED and closes the switching elements indicated by the arrows in the figure, while leaving other switching elements open. The number of the switching units used in the emitter switching unit may correspond to the maximum number of sensor drive terminals (i.e. input terminals of the emitter unit), thereby to make the emitter switching unit compatible with all possible sensors.

Figure 5:
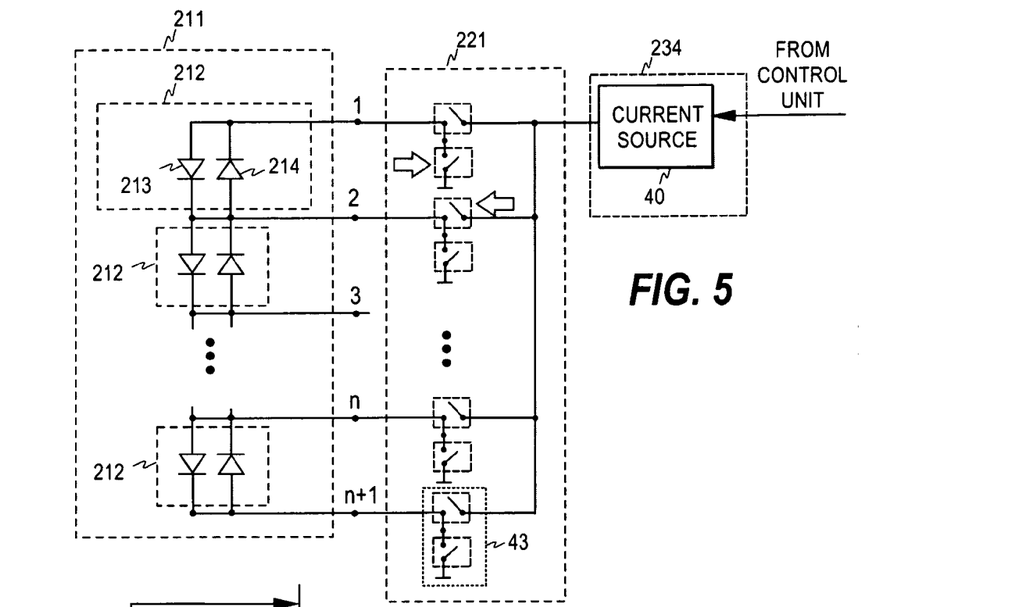
FIG. 5 illustrates one embodiment of the emitter unit and the emitter switching unit of the pulse oximeter of FIG. 2.

FIG. 5 illustrates another embodiment of the emitter unit 211 and the emitter switching unit 221 of the pulse oximeter of FIG. 2. In this case the emitter element units 212 are cascaded, i.e. the second common pole in an emitter element unit is connected to the first common pole in the next emitter element unit. Although there are still n emitter element units 212 in the embodiment of FIG. 2, the number of the input terminals of the emitter unit is now reduced to n+1. The same applies to switching units 43, i.e. the number of the output terminals of the interface unit is also n+1. The arrows indicate the two switching elements to be closed when the same LED as in the example of FIG. 4 is to be activated.

When the interface unit is provided with a dedicated memory, the information in the said memory may include sensor-specific data, general compatibility data, and possibly also emitter activation information. The sensor-specific data includes history data that is collected into the memory of the interface unit for all sensor IDs that have been used with the interface unit. The collection may be carried out by the control unit 231 of the monitoring unit. The history data may include, for example, the number of hours that the sensor has been used in the device. As discussed above, each sensor may also store the history data of its own. The general compatibility data includes information indicating the sensor types that are compatible with each possible measurement mode (wavelength set). The said data may further include data which indicates how the center wavelengths of each compatible sensor shift over time and as a function of temperature and/or how the performance of each sensor degrades over time (sensor degrade rate).

As discussed above, the emitter activation information indicates how the emitter unit is to be driven to generate an optical signal at a desired wavelength. However, if the emitter activation information is stored in the interface unit, it may include the activation information or the control codes needed for all measurement modes (i.e. for all LED control modes) possible with a plurality of monitoring units with different measurement capabilities. Each measurement mode corresponds to a specific wavelength set and the emitter activation information may include the switching control data and the drive pulse data for each set. In this way, each control unit does not have to determine the above-described control information, but may simply retrieve the said information or the control code from the interface unit memory for the wavelength combination to be employed. Furthermore, monitoring units with different measurement capabilities may utilize the same or the same type of interface unit, since they can all read the emitter activation information corresponding to their wavelength set(s). When the interface unit stores the emitter activation information for several measurement modes, the control unit may read the sensor information in the sensor memory to ascertain that the sensor is compatible with the measurement mode.

In order to utilize the sensor-specific data and the general compatibility data, the control unit may be provided with sensor diagnostic software that determines, based on the data in the interface memory and in the sensor memory, the need for informing the user about potential measurement issues, such as compatibility issues. If there is no memory in the interface unit, the above information may also be stored in the memory of the monitoring unit or in the sensor memory.

Figure 6:
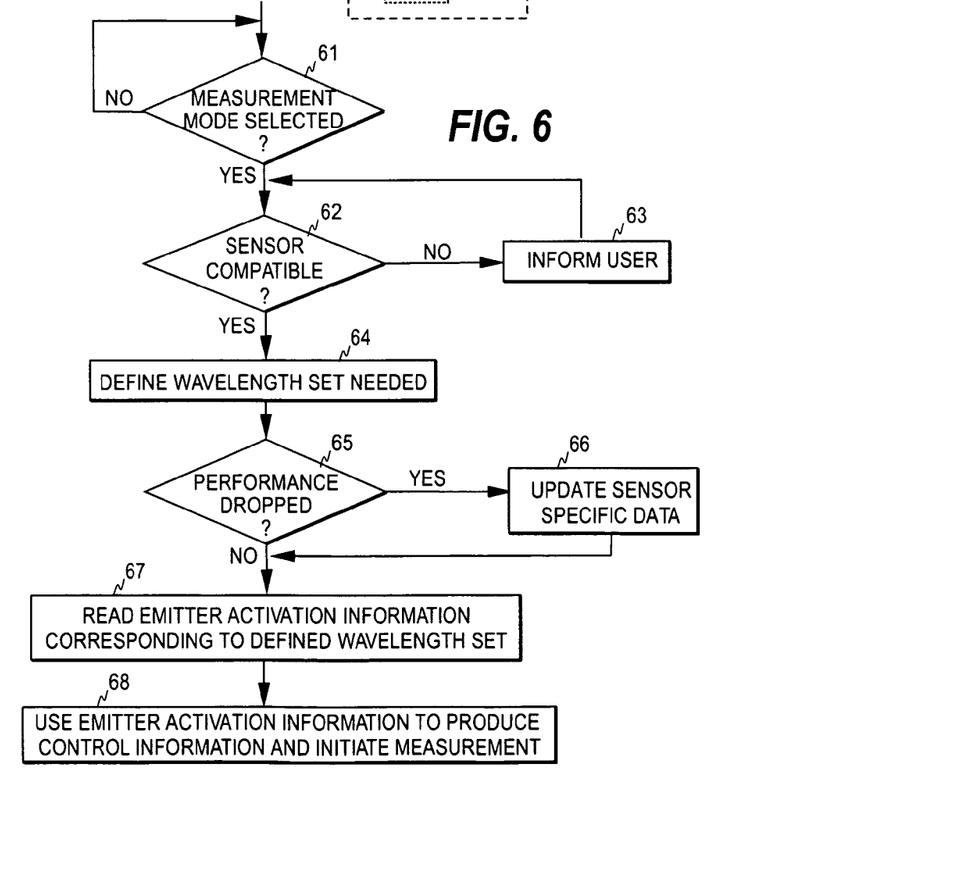
FIG. 6 is a flow diagram illustrating an example of the operation of the monitoring unit.

FIG. 6 is a flow diagram illustrating an example of the operation of the control unit prior to a measurement. When the user of the device has chosen a certain measurement mode through the user interface of the device (step 61), the control unit reads the sensor type information and the general compatibility data to determine whether a compatible sensor is connected to the device (step 62). If this not the case, the user is informed to change the sensor. This may involve displaying the sensors compatible with the selected measurement mode (step 63). When a compatible sensor is connected, the control unit determines the wavelength set to be employed (step 64) and uses the sensor-specific data and the general compatibility data, such as use hours, stored in the memory of the interface unit to determine whether the performance of the sensor has for any reason dropped below an accepted performance level (step 65). If this is the case, the control unit may perform an update of the sensor-specific data or other parameters whose values have changed (step 66). After the update of the memory data, the control unit reads the emitter activation information corresponding the combination of wavelengths to be employed (step 67), produces the control information based on the information read (step 68) and initiates the measurement. To carry out these steps, the control unit may act in several ways, depending on the location (i.e. sensor or interface unit) and content of the emitter activation information. If, for example, the emitter activation information is in the sensor and in the form of control codes, the control unit may retrieve the control code corresponding to the wavelengths to be employed and use the control code in its control software for producing the required control information for the activation of the corresponding emitter elements only.

The interface unit of FIG. 2 may further be provided with an upgrade/calibration port 223 through which the sensor memory may be read and the interface memory updated. Thus, it is also possible that the update of the sensor specific data is carried out by an external device through the upgrade/calibration port. Furthermore, in one embodiment, the sensor memory may be writable, thus allowing an update of the sensor memory and/or the upgrade of the sensor. For example, if the LEDs of the sensor are upgraded, the new information may be written into the sensor memory and into the memory of the interface unit. The update of the sensor memory may be carried out by the control unit or by an external device through port 223.

As discussed above, the general compatibility data stored in the memory of the interface unit may also be utilized by instructing the user to select the correct sensor. Upon selection of a measurement mode, the control unit may display the compatible sensor types on the screen of display 233, if a compatible sensor is not connected to the device. The control unit may store a compatibility guide that the user may use when operating the device.

Figure 7:
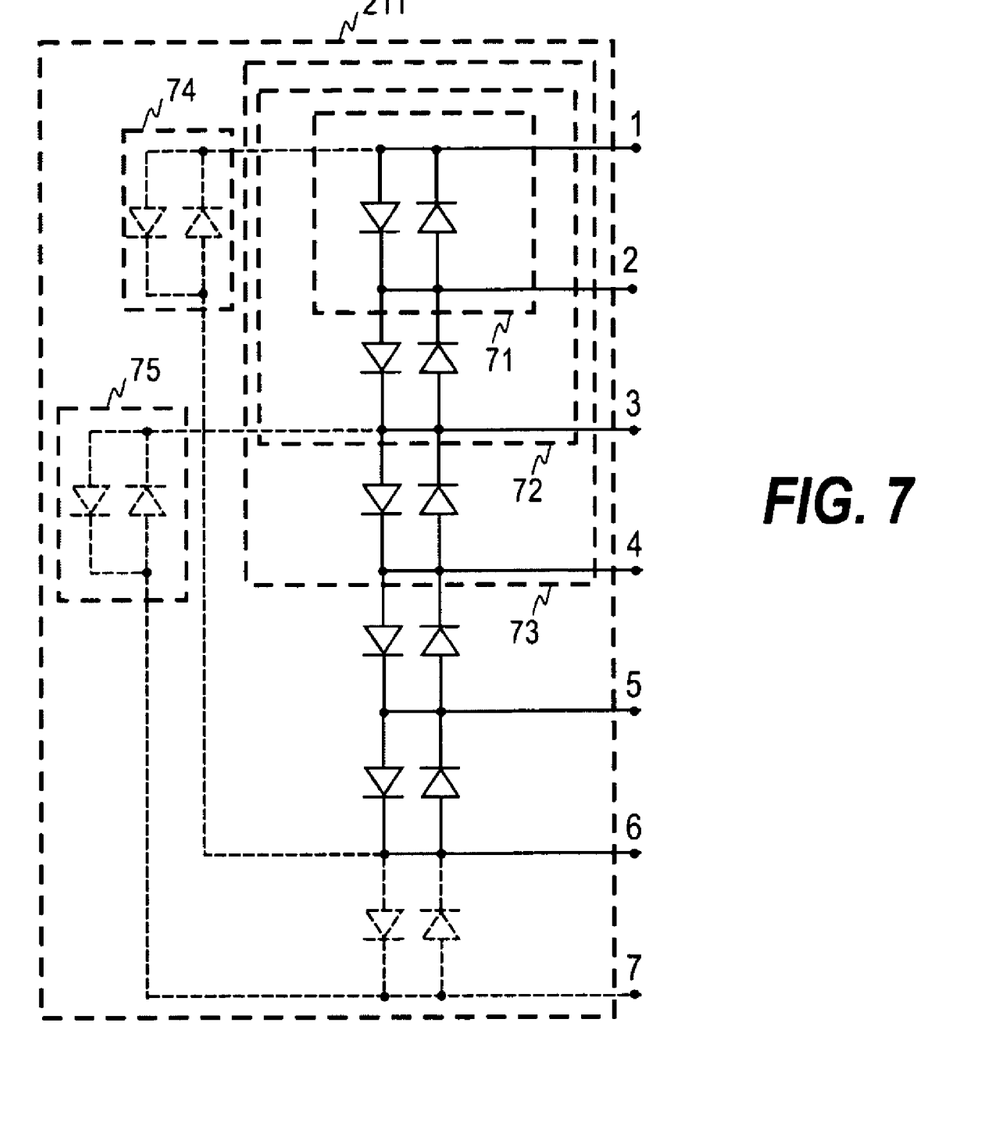
FIG. 7 illustrates a further embodiment of the emitter unit of the pulse oximeter of FIG. 2.

FIG. 7 illustrates a further example of the emitter unit of the pulse oximeter of FIG. 2. The emitter unit comprises in this case 8 emitter element units each comprising two emitter elements (LEDs or lasers) connected in parallel and back-to-back, i.e. the total number of the emitter elements is 16. However, in this case the number of the drive input terminals of the sensor unit is only 7, since two of the emitter element units, denoted with reference numbers 74 and 75, have been added in parallel with a cascade of five and four emitter element units, respectively. Additional LEDs may be added in parallel with a cascade of at least 3 or 4 LEDs, thereby to decrease the number of input terminals required in the sensor unit. However, to ensure that the drive current of such an additional LED will not leak through the cascaded LEDs connected between the same input terminals, the voltage over the activated additional LED must be less than the sum of the opening threshold voltages of the said cascaded LEDs. Therefore, the number of said cascaded LEDs must in practice be at least 3 or 4. A sensor unit comprising 2n emitter elements may thus also include less than n+1 drive input terminals. This also decreases the number of switching units 43 and the number of output terminals in the interface unit, as is obvious from FIGS. 4 and 5.

A sensor unit provided with the emitter unit of FIG. 7 may be manufactured with a full capacity of 16 emitter elements. However, the sensor unit may be used with monitoring units with different measuring capabilities. For example, the sensor unit may be used for a basic $SpO_2$ measurement (measurement mode 1) only, in which case only two emitter elements denoted with reference number 71 need to be active. The corresponding wavelengths may be, for example, 660 and 900 nm. Thus, in this case emitter activation information is needed for input terminals 1 and 2 only. If a high precision $SpO_2$ measurement (measurement mode 2) is to be taken into use, four emitter elements, denoted with reference number 72 in the figure, need to be active. In this case the emitter activation information relates to drive input terminals 1 to 3 of the sensor unit and the corresponding wavelengths may be, for example, 660, 900, 632, and 720 nm. If the sensor is to be used with a monitoring unit capable of measuring fractional oxygen saturation (measurement mode 3), at least 6 emitter elements need to be employed, which are denoted with reference number 73 in the figure. In this case, the sensor memory includes emitter activation information for at least drive input terminals 1 to 4, and the at least 6 wavelengths may be employed to track the concentrations of HbO2, HbCO, and HbMet. If the sensor is used in operating theatres in connection with major surgeries, in which blood transfusions are likely to be needed, the monitoring unit may employ 8 to 10 emitter elements to be able to follow the concentrations of total hemoglobin and hematocrit (measurement mode 4). After a certain number of use hours, the performance of the emitter elements 71 of the basic $SpO_2$ measurement is degraded so that the said elements may be replaced by new emitter elements 74 having substantially the same wavelengths. The degraded elements are inactivated by updating the emitter activation information, i.e. storing the new input terminal numbers for the said wavelengths. If the concentration of further blood substances, like glucose, is to be measured (measurement mode 5), all 16 emitter elements may be activated.

As obvious from the above, the emitter activation information may include information for all wavelengths available in the sensor or for a subset of the wavelengths available. Even though the sensor is equipped with emitter elements for all possible measurement modes, the emitter activation information may be stored for one measurement mode only, for a desired set of measurement modes, or for all possible measurement modes. Furthermore, the control unit may change the combination of wavelengths dynamically without user interaction. Depending on the blood parameters to be measured, this change of the wavelength combination may be carried out within one measurement mode or by dynamically changing the measurement mode over time. Thus, a certain measurement mode may be a combination of two or more other measurement modes or may include dynamic change of the wavelength combination as an intrinsic feature. Furthermore, it is even possible that the emitter activation information includes information for a greater number of wavelengths than the number of wavelengths currently available in the sensor, if the number of wavelengths (emitter elements) may be upgraded. However, in this case the sensor type information and the general compatibility data may reveal that the sensor in not compatible with some of the wavelengths for which activation information is stored. Based on the sensor type information and the general compatibility data the control unit may thus block the use of such extra wavelengths and inform the user of incompatibility issues relating to sensor usage. Generally, the sensor type information and the general compatibility data form a set of compatibility information based on which the monitoring unit may pre-check the compatibility of the sensor unit with any combination of wavelengths intended to be employed in the apparatus. Furthermore, based on the emitter activation information read from the sensor and the compatibility information stored elsewhere in the apparatus, the monitoring unit may guide the user to select a compatible sensor by displaying instructive messages, for example.

To increase compatibility, a multiwavelength monitoring unit 230 may be made compatible with a standard two-wavelength sensor, since the pin order of terminal 250 may be such that the said standard sensor may be connected directly to connector 250. In this case, the interface unit is not needed.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A measuring apparatus for determining the amount of at least one substance in blood of a subject, the measuring apparatus comprising:
    a sensor unit comprising
        an emitter unit comprising a first plurality of emitter elements configured to emit radiation at a second plurality of wavelengths; and
        a detector unit configured to receive radiation generated by the emitter elements and transmitted through tissue of a subject, wherein the detector unit is further configured to produce electric measurement signals indicative of absorption caused by blood of the subject;
    a first memory storing emitter activation information for at least a third plurality of wavelengths, wherein the third plurality of wavelengths belongs to the second plurality of wavelengths, and wherein the emitter activation information indicates, for each wavelength in the third plurality of wavelengths, input terminals of the sensor unit to which the corresponding emitter element is connected; and
    a monitoring unit configured to process the electric measurement signals, wherein the monitoring unit is further configured to produce, based on the emitter activation information, control information for employing a desired combination of wavelengths selected from the third plurality of wavelengths.

2. The measuring apparatus according to claim 1, wherein the first memory is in the sensor unit.

3. The measuring apparatus according to claim 1, wherein the emitter activation information indicates, for each wavelength in the third plurality of wavelengths, a polarity of current to be supplied to said input terminals.

4. The measuring apparatus according to claim 1, wherein the emitter activation information comprises at least one control code, and wherein each control code is linked to the control information required to employ a particular combination of wavelengths.

5. The measuring apparatus according to claim 2, wherein the emitter unit comprises at most n+1 input terminals and the first plurality of emitter elements comprises 2n emitter elements.

6. The measuring apparatus according to claim 1, further comprising an interface unit operably connected between the sensor unit and the monitoring unit.

7. The measuring apparatus according to claim 6, wherein the first memory is in the interface unit.

8. The measuring apparatus according to claim 6, wherein the monitoring unit comprises a single drive current source operably connectable to an emitter switching unit in the interface unit.

9. The measuring apparatus according to claim 1, wherein the monitoring unit is further configured to change the desired combination of wavelengths in time domain.

10. The measuring apparatus according to claim 1, wherein the monitoring unit is further configured to pre-check compatibility of the sensor unit with any combination of wavelengths intended to be employed in the measuring apparatus.

11. A physiological sensor for use in determining the amount of at least one substance in blood of a subject, the physiological sensor being attachable to the subject and comprising:
    an emitter unit comprising a first plurality of emitter elements configured to emit radiation at a second plurality of wavelengths;
    a sensor memory storing emitter activation information for at least a third plurality of wavelengths, thereby to enable a monitoring unit operably connectable to the physiological sensor to employ a desired combination of wavelengths selected from the third plurality of wavelengths, wherein the third plurality of wavelengths belongs to the second plurality of wavelengths, and wherein the emitter activation information indicates, for each wavelength in the third plurality of wavelengths, input terminals of the sensor corresponding to which the required emitter element is connected; and
    a detector unit configured to receive radiation generated by the emitter elements and transmitted through tissue of the subject, wherein the detector unit is further configured to produce electric measurement signals indicative of absorption caused by blood of the subject.

12. The sensor according to claim 11, wherein the emitter activation information indicates, for each wavelength in the third plurality of wavelengths, a polarity of current to be supplied to said input terminals.

13. The sensor according to claim 12, wherein the emitter activation information comprises an extinction matrix including extinction coefficients for a plurality of blood substances.

14. The sensor according to claim 11, wherein the emitter activation information comprises at least one control code, and wherein each control code is linked to the control information required to employ a particular combination of wavelengths belonging to the third plurality of wavelengths.

15. The sensor according to claim 11, wherein the first plurality of emitter elements comprises 2n emitter elements and the emitter unit comprises at most n+1 input terminals.

16. The sensor according to claim 11, wherein the sensor memory stores the emitter activation information for the third plurality of wavelengths and wherein the third plurality of wavelengths equals to the second plurality of wavelengths.

17. The sensor according to claim 16, wherein the first plurality of emitter elements is greater than the second plurality of wavelengths.

18. A sensor arrangement for use in determining the amount of at least one substance in blood of a subject, the sensor arrangement comprising:
- a sensor unit comprising a first plurality of emitter elements configured to emit radiation at a second plurality of wavelengths; and
- an interface unit comprising:
- a first interface for connecting the interface unit to a monitoring unit;
- a second interface connected to the sensor unit;
- an emitter switching unit configured to connect drive current generated by the monitoring unit to the sensor unit through the second interface; and
- a memory storing emitter activation information for at least a third plurality of emitter elements, thereby to enable the monitoring unit to employ a desired combination of wavelengths selected from the third plurality of wavelengths, and wherein the emitter activation information indicates, for each wavelength in the third plurality of wavelengths, input terminals of the sensor unit to which the corresponding emitter element is connected, wherein the third plurality of wavelengths belongs to the second plurality of wavelengths.

19. The interface unit according to claim 18, wherein the emitter activation information comprises at least one control code, and wherein each control code is linked to the control information required to employ a particular combination of wavelengths selected from the third plurality of wavelengths.

20. The interface unit according to claim 19, wherein the at least one control code comprises a plurality of control codes for multiple monitoring units with different measuring capabilities.

* * * * *